United States Patent
Bruno et al.

(10) Patent No.: US 9,540,229 B2
(45) Date of Patent: Jan. 10, 2017

(54) PACKAGED SENSOR ASSEMBLY

(71) Applicant: STMICROELECTRONICS S.R.L., Agrate Brianza (IT)

(72) Inventors: Giuseppe Bruno, Paterno' (IT); Sebastiano Conti, Pregnana Milanese (IT); Mario Chiricosta, Tremestieri Etneo (IT); Michele Vaiana, San Giovanni la Punta (IT); Calogero Marco Ippolito, Aci Castello (IT); Mario Maiore, Aci Sant'Antonio (IT); Daniele Casella, Francofonte (IT)

(73) Assignee: STMicroelectronics S.r.l., Agrate Brianza (IT)

( * ) Notice: Subject to any disclaimer, the term of this patent is extended or adjusted under 35 U.S.C. 154(b) by 0 days.

(21) Appl. No.: 14/962,945

(22) Filed: Dec. 8, 2015

(65) Prior Publication Data

US 2016/0347606 A1    Dec. 1, 2016

(30) Foreign Application Priority Data

May 29, 2015   (IT) .................. 102015000019550

(51) Int. Cl.
*B81B 7/00*   (2006.01)

(52) U.S. Cl.
CPC ........ *B81B 7/007* (2013.01); *B81B 2201/0264* (2013.01); *B81B 2201/0292* (2013.01); *B81B 2207/094* (2013.01)

(58) Field of Classification Search
CPC ............... B81B 7/007; B81B 2207/094; B81B 2201/0292; B81B 2201/0264
See application file for complete search history.

(56) References Cited

U.S. PATENT DOCUMENTS

| | | | |
|---|---|---|---|
| 9,233,834 B2* | 1/2016 | Faralli | .................. B81B 3/0021 |
| 2010/0148950 A1 | 6/2010 | Yamaguchi et al. | |
| 2014/0116122 A1 | 5/2014 | Lammel et al. | |
| 2014/0319630 A1 | 10/2014 | Conti et al. | |
| 2015/0001645 A1 | 1/2015 | Faralli et al. | |

FOREIGN PATENT DOCUMENTS

| | | |
|---|---|---|
| CN | 104779213 A | 7/2015 |
| WO | 2013/156539 A1 | 10/2013 |
| WO | 2014066768 A2 | 5/2014 |

* cited by examiner

*Primary Examiner* — David Vu
(74) *Attorney, Agent, or Firm* — Seed Intellectual Property Law Group LLP

(57) ABSTRACT

A packaged sensor assembly includes: a packaging structure, having at least one opening; a humidity sensor and a pressure sensor, which are housed inside the packaging structure and communicate fluidically with the outside through the opening, and a control circuit, operatively coupled to the humidity sensor and to the pressure sensor; wherein the humidity sensor and the control circuit are integrated in a first chip, and the pressure sensor is integrated in a second chip distinct from the first chip and bonded to the first chip.

23 Claims, 4 Drawing Sheets

PACKAGED SENSOR ASSEMBLY

BACKGROUND

Technical Field

The present disclosure relates to a packaged sensor assembly.

Description of the Related Art

As is known, attention to the development and integration of microelectromechanical environmental sensors is progressively increasing as the use of portable electronic devices, such as smartphones and tablets or other so-called "wearable" electronic devices, increases. In particular, there is noted a specific interest to enclose a microelectromechanical pressure sensor and a microelectromechanical humidity sensor within a single packaging structure for electronic devices, together with a control circuit such as an application-specific integrated circuit (ASIC). The control circuit may serve for controlling operation of the sensors and as an interface for converting the electrical signals supplied by the sensors into data that may be used by further processing stages for performing various functions.

A microelectromechanical pressure sensor generally comprises a flexible membrane, suspended over a cavity in a semiconductor substrate. The membrane is deformed by the pressure difference between the two sides. Sensitive elements, in general of a piezoelectric type, are coupled to the faces of the membrane and enable detection of the degree of deformation.

Microelectromechanical humidity sensors are, instead, usually of a capacitive type and comprise electrodes coupled together to form a capacitor and separated by a hygroscopic polymer, the dielectric constant of which varies as a function of the humidity absorbed.

A problem generally to be tackled in the integration process is determined by the contrasting application preferences of pressure sensors on the one hand and humidity sensors on the other. Both types of sensors, in fact, have to be exposed to external environmental conditions through openings in the packaging structure to be in condition of operating correctly. However, for humidity sensors it is important to maximize exposure to the external environment to favor absorption of humidity by the hygroscopic polymer, while pressure sensors prefer protection from electromagnetic radiation in the spectrum of the visible and of the infrared. In fact, incident radiation causes parasitic currents and consequent voltage drops that may alter the useful signals. Exposure to the external environment is therefore preferred to be sufficient to provide suitable fluidic connection therewith and, at the same time, should minimize the intensity of incident radiation on the membrane and, in particular, on the piezoresistive elements.

In addition to the desire to balance the contrasting preferences for pressure sensors and humidity sensors, it is also desirable to satisfy the general tendency to reduce the dimensions of devices and of the packaging structure as a whole, to render use of electronic devices more flexible and convenient.

BRIEF SUMMARY

One or more embodiments of the present disclosure is to provide a packaged sensor assembly.

One embodiment of the present disclosure is directed to a packaged sensor assembly including a packaging structure having an opening. The sensory assembly further includes a first semiconductor chip that integrates a humidity sensor and a control circuit. The control circuit is operatively coupled to the humidity sensor. The humidity sensor is housed inside the packaging structure and in fluid communication with an environment external to the sensor assembly through the opening. The sensor assembly further includes a second semiconductor chip that integrates a MEMS pressure sensor bonded to the first semiconductor chip. The pressure sensor is operatively coupled to control circuit. The pressure sensor is housed inside the packaging structure and in fluid communication with the environment external to the sensor assembly through the opening.

BRIEF DESCRIPTION OF THE SEVERAL VIEWS OF THE DRAWINGS

For a better understanding of the disclosure, some embodiments thereof will now be described purely by way of non-limiting example and with reference to the attached drawings, wherein.

DETAILED DESCRIPTION

Figure 1:
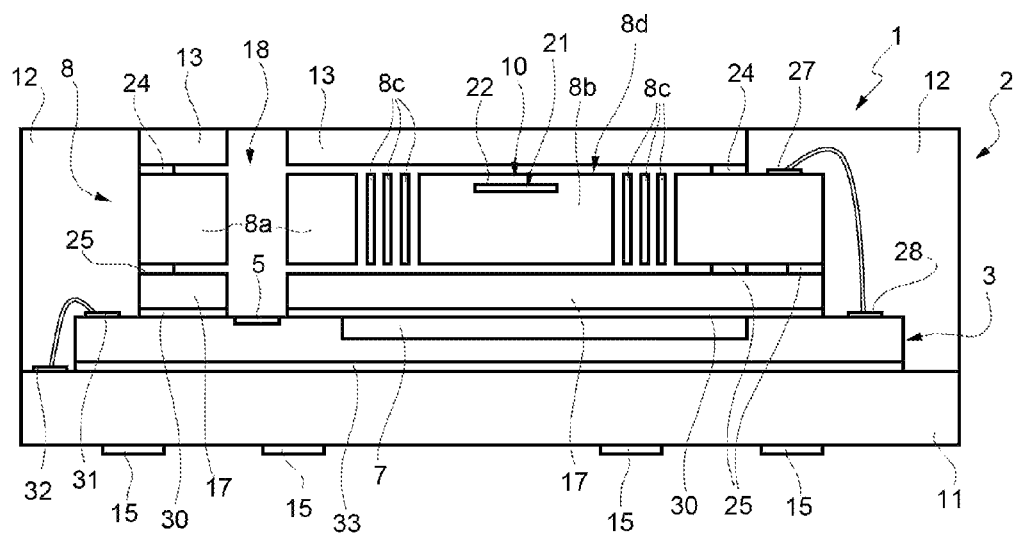
FIG. 1 is a cross-sectional view of a packaged sensor assembly according to one embodiment of the present disclosure.

With reference to FIG. 1, a packaged sensor assembly according to one embodiment of the present disclosure is designated as a whole by 1 and comprises a packaging structure 2, a first chip 3, in which a humidity sensor 5 and a control circuit or ASIC 7 are integrated, and a second chip 8, in which an electromechanical transducer, such as a pressure sensor 10, is integrated.

The packaging structure 2 is of a molded type, for example of the land grid array (LGA) type, and comprises a substrate 11, a lateral structure 12, and a first cap 13. The substrate 11 is made, for example, of FR-4 and is provided with metal contact pads or lands 15 on an outer face. The lateral structure 12 may be made of resin and surrounds the first chip 3 and the second chip 8. In one embodiment, the lateral structure 12 is obtained by molding, for example using a technique of transfer molding, in particular film-assisted molding.

The first cap 13 defines a wall of the packaging structure 2 opposite to the substrate 11 and forms a die with the first chip 3, the second chip 8, and a second cap 17.

An opening 18 in the first cap 13 sets the inside of the packaging structure 2 in fluidic communication with an environment outside the package. The opening 18 is configured to enable air external to the package to exchange within the packaging structure 2 so that the humidity sensor 5 is reached in a short time by a gaseous mixture in which the packaged sensor assembly 1 is immersed. In one embodiment, the dimensions of the opening 18 are equal to or greater than the dimensions of the humidity sensor.

Figure 2:
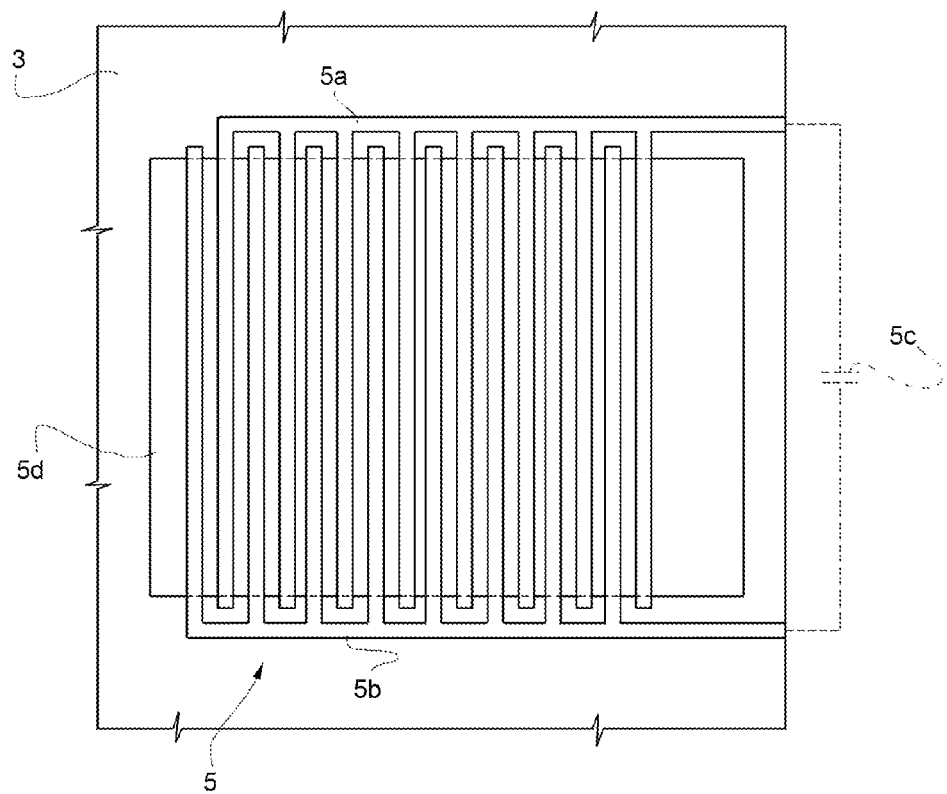
FIG. 2 is a top plan view of an enlarged detail of the packaged sensor assembly of FIG. 1.

The humidity sensor 5 is based upon MEMS (microelectromechanical systems) technology and, in one embodiment, is of a capacitive type. For instance (FIG. 2), the humidity sensor 5 comprises first electrodes 5a and second electrodes 5b comb-fingered and coupled together to form a capacitor 5c. The space between the first electrodes 5a and the second electrodes 5b is at least in part occupied by a dielectric region 5d of hygroscopic material, the electrical permittivity of which is a function of the humidity absorbed. In one embodiment, the dielectric region 5d is made of polyimide. With reference once again to FIG. 1, the humidity sensor 5 is integrated in the first chip 3, together with the control circuit 7, and is aligned to the opening 18 in the first cap 13.

Figure 3:
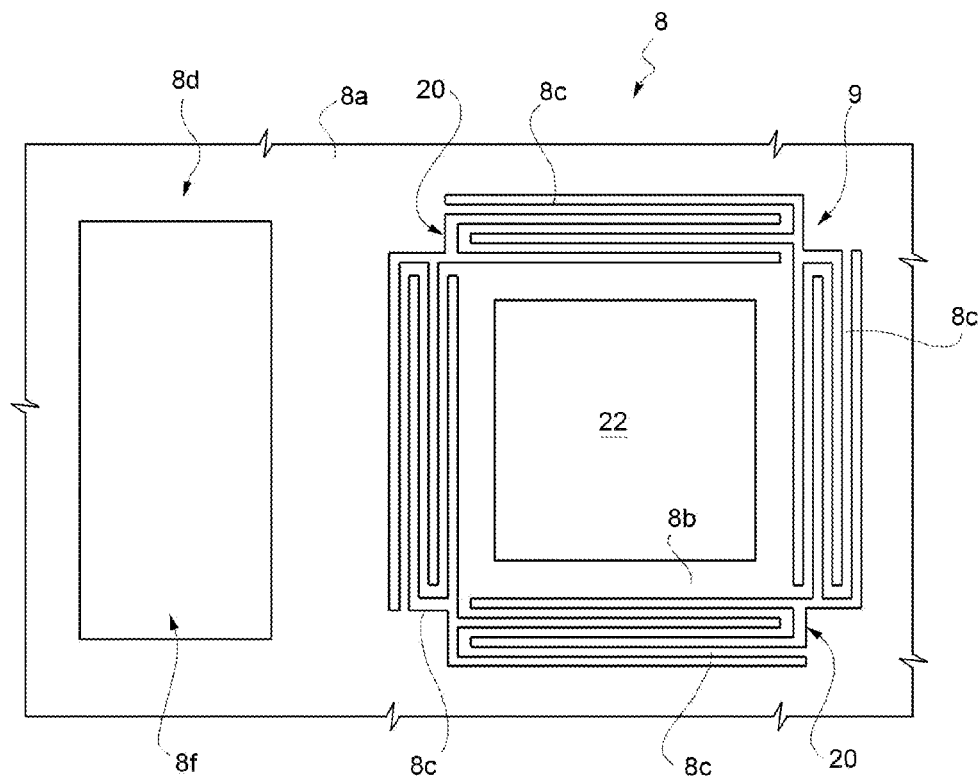
FIG. 3 is a top plan view of a component of the packaged sensor assembly of FIG. 1.
Figure 4:
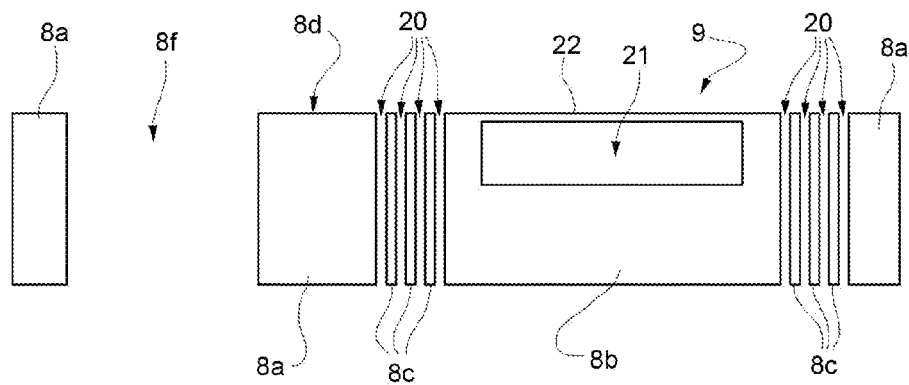
FIG. 4 is an enlarged cross-sectional view of the component of FIG. 3.

In one embodiment, the pressure sensor 10 is a microelectromechanical membrane sensor, with piezoelectric type or capacitive type detection, for example (see also FIGS. 3 and 4). As already mentioned, the pressure sensor 10 is integrated in the second chip 8. The second chip 8 comprises a frame-like supporting portion 8a, a sensor portion 8b, and elastic connection elements 8c that connect the sensor portion 8b elastically to the supporting portion 8a. The supporting portion 8a and the sensor portion 8b are separated by a through trench 20, extending across which are the elastic connection elements 8c. The sensor portion 8b, which is, for example, quadrangular in shape, has a cavity 21 sealed on one side by a membrane 22 that defines a portion of a face 8d of the second chip 8. The elastic connection elements 8c are configured to enable relative movements of the sensor portion 8b with respect to the supporting portion 8a, in particular translations in two independent directions parallel to the face 8d and rotations about axes perpendicular to the face 8d. The elastic connection elements 8c enable accommodation of the effects of thermal expansion, of deformations, and of mechanical stresses that may arise during the packaging steps and during the useful service life of the sensor assembly 1.

With reference once again to FIG. 1, the second chip 8 is sandwiched between the first cap 13 and the second cap 17. More precisely, the face 8d of the second chip 8 is bonded to the first cap 13 by bonding regions 24, whereas a face 8e, opposite to the face 8d, is bonded to the second cap 17 by bonding regions 25. The bonding regions 24, 25 are, for example, of a type used in wafer-to-wafer bonding techniques and, according to the technique specifically used, may have a thickness, for example, between 3 μm and 50 μm. The membrane 22 of the pressure sensor 10 thus faces the first cap 13, from which it is separated by a distance substantially equal to the thickness of the bonding regions 24. In addition, the membrane 22 is arranged facing the opposite side with respect to the first chip 3, in which the humidity sensor 5 and the control circuit 7 are integrated.

The second chip 8 projects laterally with respect to the first cap 13 and houses pads 27 for electrical connection to the control circuit 7 by wire bonding with respective pads 28 on the first chip 3.

Using for example an adhesive layer 30, the second cap 17 is bonded to the first chip 3, which projects laterally for housing the pads 28 and further pads 31 for connection with respective pads or paths 32 on the substrate 11 by wire bonding. The wire bondings between the pads 27 and the pads 28 and the wire bondings between the pads 31 and the paths 32 are incorporated in the lateral structure 12. The paths 32 are located on the face of the substrate 11 bonded to the first chip 3 and are in turn coupled, by through connections (not shown), to respective contact pads 15 on the outer face of the substrate 11.

The first chip 3 is finally bonded to the substrate 11 through an adhesive layer 33.

The supporting portion 8a of the second chip 8 and the second cap 17 have respective through openings aligned to the opening 18 in the first cap 13 (the opening in the supporting portion 8a is designated by 8f in FIGS. 3 and 4). In one embodiment, the openings of the supporting portion 8a of the second chip 8 and of the second cap 17 have the same dimensions as the opening 18 in the first cap 18 and as the humidity sensor 5. Also the adhesive layer 30 is interrupted in a region corresponding to the humidity sensor 5, which is thus exposed to the external atmosphere through a direct path. Advantageously, instead, the openings are provided at a distance from the pressure sensor 10, in particular, as regards the second chip 8, in the supporting portion 8a. The pressure sensor 10 thus communicates with the outside through a gap between the second chip 8 and the first cap 13, which has the thickness of the bonding regions 24. The gap enables the membrane 22 to be kept at the external atmospheric pressure, without there being a significant exposure to light radiation. In particular, direct exposure is prevented or minimized such that only a small fraction of the radiation that enters from the opening 18 may reach the membrane through multiple reflections along the gap between the second chip 8 and the first cap 13.

Another advantage of the sensor assembly 1 is represented by the connection of the sensor portion 8b of the second chip 8 to the supporting portion 8a by the elastic connection elements 8c. This type of connection, in fact, affords a good level of mechanical decoupling between the supporting portion 8a and the sensor portion 8b. The stresses that are frequently set up during the packaging steps or as a result of thermal and mechanical stresses are absorbed by the elastic connection elements 8c and are not transmitted to the membrane 22. The membrane 22 is thus free from stresses that might affect its natural deformations and, consequently, the process of electromechanical transduction of the pressure. The use of the elastic elements 8c enables in particular incorporation of the second chip 8 with the pressure sensor 10 in a molded packaging structure, instead of in a structure of the cavity type. The benefit reflects especially on the dimensions of the sensor assembly as a whole and on abatement of light radiation incident on the pressure sensor.

Figure 5:
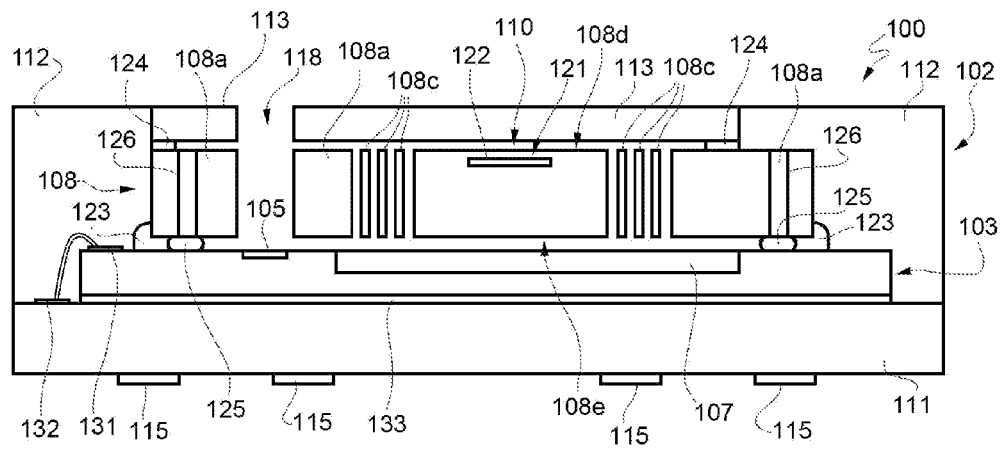
FIG. 5 is a cross-sectional view of a packaged sensor assembly according to a different embodiment of the present disclosure.

FIG. 5 illustrates a different embodiment of the present disclosure. In this case, a packaged sensor assembly 100 comprises a packaging structure 102, a first chip 103, in which a humidity sensor 105 and a control circuit 107 are integrated, and a second chip 108, in which a pressure sensor 110 is integrated.

The humidity sensor 105 and the pressure sensor 110 are of the type already described with reference to FIGS. 1-4. In particular, the pressure sensor 110 is integrated in the second chip 108, which comprises a supporting portion 108a, a sensor portion 108b connected to the supporting portion 108a by elastic connection elements 108c, and a membrane 122 that extends so to close a cavity 121 and defines a portion of a face 108d of the second chip 108.

The packaging structure 102 is of a molded type, for example of the LGA type, and comprises a substrate 111, a lateral structure 112, and a cap 113. The substrate 111 is made, for example, of FR-4 and is provided with metal contact pads or lands 115 on an outer face. The lateral structure 112 may be obtained by molding resin and surrounds the first chip 103 and the second chip 108.

A cap 113 defines a wall of the packaging structure 102 opposite to the substrate 111 and forms a die with the first chip 103 and the second chip 108.

The inside of the packaging structure 102 is in fluidic communication with the environment outside of the package through an opening 118 in the cap 113. The opening 118, of dimensions substantially equal to those of the humidity sensor 105, enables air external to the package to exchange within the packaging structure 102 so that the humidity sensor 105 is reached in a short time by the gaseous mixture in which the packaged sensor assembly 100 is immersed.

The face 108d of the second chip 108 is bonded to the cap 113 by bonding regions 124, whereas a face 108e, opposite to the face 108d, is bonded to the first chip 103 by conductive bonding regions 125. In this case, the first chip 103 functions as protective cap for the pressure sensor 110. The bonding regions 124 are, for example, of a type used in wafer-to-wafer bonding techniques. The bonding regions 125, instead, may be of a type used in ball bonding techniques and enable electrical coupling between the pressure sensor 110 and the control circuit 107. The electrical connection between the structures on the face 108d of the second chip 108 and the bonding regions 125 is obtained with conductive through silicon vias (TSVs) 126. A layer of filler material 123 surrounds and seals the second chip 108 to prevent the liquid resin from penetrating between the first chip 103 and the second chip 108 during fabrication by molding of the lateral structure 112.

The supporting portion 108a of the second chip 108 has a through opening aligned with the opening 118 in the cap 113. Also in this embodiment, the pressure sensor 110 is located at a distance from the opening 118 and is accessible through a gap between the second chip 108 and the cap 113, of a thickness equal to the thickness of the bonding regions 124. The gap is sufficient for setting the pressure sensor 110 in fluidic communication with the environment outside of the package and, at the same time, eliminates or at least reduces substantially the incident light radiation.

The first chip 103 is bonded to the substrate 111 by an adhesive layer 133. The humidity sensor 105 is aligned to the opening 118 and to the opening in the supporting portion 108a of the second chip 108 and is thus exposed to the external atmosphere.

The first chip 103 projects laterally with respect to the second chip 108 for housing pads 131 for connection with respective pads or paths 132 on the substrate 111 by wire bonding, which are incorporated in the lateral structure 112. The paths 132 are located on the face of the substrate 111 bonded to the first chip 103 and are in turn coupled, by through connections (not shown), to respective contact pads 115 on the outer face of the substrate 111.

The sensor assembly 100 utilizes one protective cap for the pressure sensor 110, since on one side, the first chip 103 has the purpose of providing protection. The overall thickness of the sensor assembly 100 is thus advantageously reduced.

Figure 6:
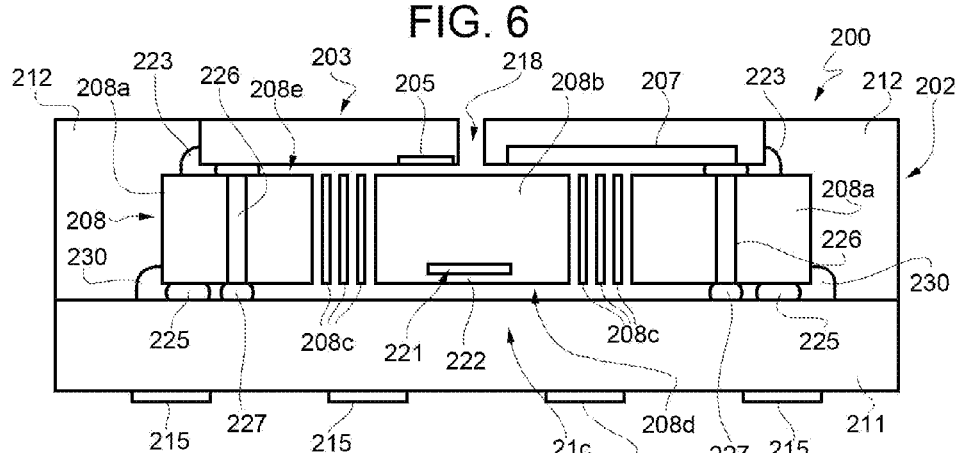
FIG. 6 is a cross-sectional view of a packaged sensor assembly according to a further embodiment of the present disclosure.

With reference to FIG. 6, a packaged sensor assembly 200 according to one embodiment of the present disclosure comprises a packaging structure 202, a first chip 203, in which a humidity sensor 205 and a control circuit 207 are integrated, and a second chip 208, in which a pressure sensor 210 is integrated.

The humidity sensor 205 and the pressure sensor 210 are of the type already described with reference to FIGS. 1-4. In particular, the pressure sensor 210 is integrated in the second chip 208, which comprises a supporting portion 208a, a sensor portion 208b connected to the supporting portion 208a by elastic connection elements 208c, and a membrane 222, which closes a cavity 221 and defines a portion of a face 208d of the second chip 208.

The packaging structure 202 is of a molded type, for example of the LGA type, and comprises a substrate 211 and a lateral structure 212. The first chip 203 forms an integral part of the packaging structure 202, of which it defines a protective cap. The substrate 211 is made, for example, of FR-4 and is provided with metal contact pads or lands 215 on an outer face. The lateral structure 212 may be obtained by molding resin. The first chip 203 is arranged for closing the lateral structure 212 and has an opening 218 that sets the inside of the packaging structure 202 in communication with the environment outside of the package. In the embodiment of FIG. 6, the opening 218 is arranged at the center with respect to the first chip 203. However, in other embodiments (not illustrated) the opening may be off-center. The opening 218 may be obtained with a step of dry chemical etching carried out following upon steps of production of electronic components, for example with a CMOS process, to obtain the control circuit 207.

The humidity sensor 205 is arranged on the face of the first chip 203 facing the inside of the packaging structure 202, in the immediate vicinity of the opening 218.

The first chip 203 is bonded to a face 208e of the second chip 208 by conductive bonding regions 224, which enable electrical connection. The face 208e is opposite to the face 208d on which the membrane 222 is located. In one embodiment, further, the second chip 208 is provided with conductive through vias 226, which enable electrical connection of the bonding regions 224 to pads 227 on an inner face of the substrate 211.

The second chip 208 is bonded to the substrate 211 by conductive bonding regions 225. The pads 227 and the bonding regions 225 are coupled to respective contact pads 215 on the outer face of the substrate 211. Further, the second chip 208 is oriented so that the membrane 222 faces the substrate 211, on the side opposite to the opening 218.

A layer of filler material 223 surrounds the first chip 203 at the interface with the second chip 208 and seals the gaps between the first chip 203 and the second chip 208. Likewise, a layer of filler material 230 surrounds the second chip 208 at the interface with the substrate 211 and seals the gaps between the second chip 208 and the substrate 211.

Figure 7:
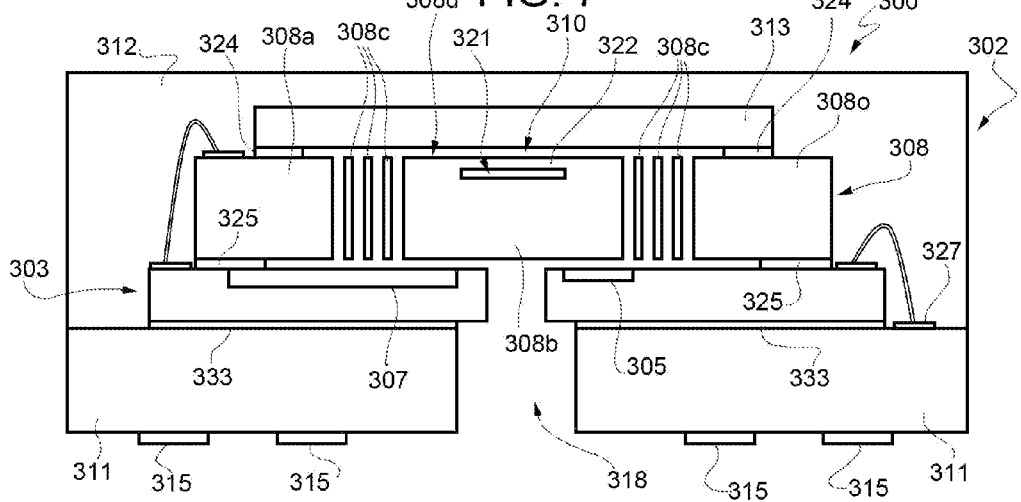
FIG. 7 is a cross-sectional view of a packaged sensor assembly according to yet a further embodiment of the present disclosure.

According to a further embodiment of the present disclosure, illustrated in FIG. 7, a packaged sensor assembly 300 comprises a packaging structure 302, a first chip 303, in which a humidity sensor 305 and a control circuit 307 are integrated, and a second chip 308, in which a pressure sensor 310 is integrated.

The humidity sensor 305 and the pressure sensor 310 are of the type already described with reference to FIGS. 1-4. In particular, the pressure sensor 310 is integrated in the second chip 308, which comprises a supporting portion 308a, a sensor portion 308b connected to the supporting portion 308a by elastic connection elements 308c, and a membrane 322, which closes a cavity 321 and defines a portion of a face 308d of the second chip 308.

The packaging structure 302 is of a molded type, for example of the LGA type, and comprises a substrate 311 and a cap 312. The substrate 311 is made, for example, of FR-4 and is provided with metal contact pads or lands 315 on an outer face. The cap 312 may be obtained by molding resin and englobes the first chip 303 and the second chip 308.

The first chip 303 is bonded to the substrate 311 with an adhesive layer 333 and is electrically connected to pads 327 on the substrate 311 by wire bonding.

An opening 318 through the substrate 311 and the first chip 303 sets the inside of the packaging structure 302 in fluidic communication with the environment outside of the package. In the embodiment of FIG. 7, the opening 318 is arranged at the center with respect to the substrate 311 and to the first chip 303. In other embodiments (not illustrated), however, the opening may be off-center.

The second chip 308 is sandwiched between a cap 313 and the first chip 303 and is bonded thereto by bonding regions 324 and bonding regions 325. Further, the second chip 308 is electrically coupled to the first chip 302 by wire bondings.

The second chip 308 is oriented so that the membrane 322 faces the cap 311, thus on a side opposite to the opening 318.

Figure 8:
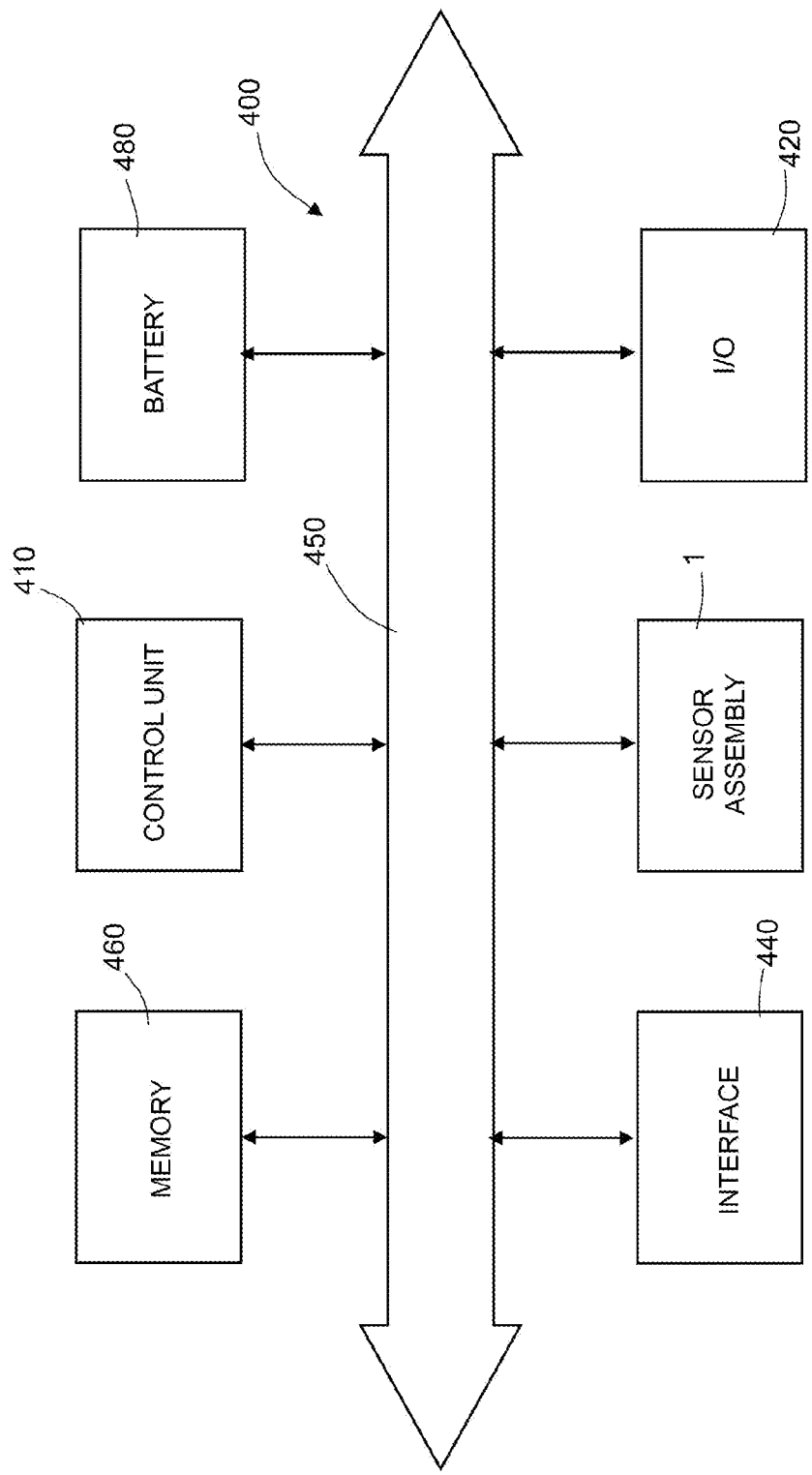
FIG. 8 is a simplified block diagram of an electronic system incorporating a packaged sensor assembly according to an embodiment of the present disclosure.

FIG. 8 illustrates a portion of an electronic system 400 according to one embodiment of the present disclosure. The system 400 incorporates the sensor assembly or electromechanical transducer 1 and may be used in devices such as, for example, a laptop computer or tablet, possibly with wireless-connection capacity, a cellphone, a smartphone, a messaging device, a digital music player, a digital camera, or other devices designed to process, store, transmit, or receive information. In particular, the electroacoustic transducer 1 may be used for providing voice-control functions, for example, in a motion-activated user interface for computers or consoles for videogames or in a satellite-navigation device.

The electronic system 400 may comprise a control unit 410, an input/output (I/O) device 420 (for example, a keyboard or a display), the electroacoustic transducer 1, a wireless interface 440, and a memory 460, of a volatile or non-volatile type, which are coupled together through a bus 450. In one embodiment, a battery 480 may be used for supplying electrically energy to the system 400. It should be noted that the scope of the present disclosure is not limited to embodiments that present necessarily one or all of the devices listed.

The control unit 410 may comprise, for example, one or more microprocessors, microcontrollers, and the like.

The I/O device 420 may be used for generating a message. The system 400 may use the wireless interface 440 for transmitting and receiving messages to and from a wireless communication network with a radio-frequency (RF) signal. Examples of wireless interface may comprise an antenna, a wireless transceiver, such as a dipole antenna, even though the scope of the present disclosure is not limited from this standpoint. In addition, the I/O device 420 may supply a voltage representing what is stored either in the form of digital output (if digital information has been stored) or in the form of analog output (if analog information has been stored).

The electronic system 400 may be any electronic system, such as portable electronic devices, such as smartphones, cameras, video recording devices, tablets, wearable devices, such as smart watches, or any other electronic device.

Finally, it is evident that modifications and variations may be made to the device and to the method described, without thereby departing from the scope of the present disclosure.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A packaged sensor assembly comprising:
 a packaging structure having an opening;
 a first semiconductor chip that integrates a humidity sensor and a control circuit operatively coupled to the humidity sensor, the humidity sensor housed inside the packaging structure and in fluid communication with an environment external to the sensor assembly through the opening; and
 a second semiconductor chip that integrates a MEMS pressure sensor bonded to the first semiconductor chip, the pressure sensor operatively coupled to the control circuit, the pressure sensor housed inside the packaging structure and in fluid communication with the environment external to the sensor assembly through the opening.

2. The sensor assembly according to claim 1, wherein the pressure sensor includes a membrane delimiting a cavity in the second semiconductor chip.

3. The sensor assembly according to claim 2, wherein the second semiconductor chip includes a supporting portion and a sensor portion, the sensor portion integrating the membrane, the membrane coupled to the supporting portion by elastic connection elements.

4. The sensor assembly according to claim 3, wherein the elastic connection elements are configured to enable relative movements of the sensor portion with respect to the supporting portion in two independent directions parallel to a face of the second semiconductor chip and rotations about axes perpendicular to the face.

5. The sensor assembly according to claim 3, wherein the packaging structure includes a substrate and a first cap.

6. The sensor assembly according to claim 5, wherein the first semiconductor chip is arranged between the second semiconductor chip and the substrate.

7. The sensor assembly according to claim 5, wherein:
 the first cap is bonded to a face of the second semiconductor chip, wherein the opening is provided in the first cap;
 the humidity sensor is exposed by the opening in the first cap; and
 the supporting portion of the second semiconductor chip has a respective through opening aligned to the opening in the first cap.

8. The sensor assembly according to claim 7, comprising a second cap arranged between the first semiconductor chip and the second semiconductor chip and has a respective opening aligned to the opening in the first cap.

9. The sensor assembly according to claim 5, wherein the opening is a first opening and provided in the substrate, and the first semiconductor chip includes a second opening at least partially aligned with the first opening.

10. The sensor assembly according to claim 5, wherein the membrane faces the first cap.

11. The sensor assembly according to claim 5, wherein the second semiconductor chip is arranged between the first semiconductor chip and the substrate, and the first cap is defined by the first semiconductor chip.

12. The sensor assembly according to claim 5, wherein the opening is provided in the first semiconductor chip.

13. The sensor assembly according to claim 12, wherein the second semiconductor chip includes conductive through vias and the first semiconductor chip is electrically coupled to conductive structures on the substrate through the conductive through vias.

14. The sensor assembly according to claim 2, wherein the membrane is at a face of the second semiconductor chip opposite to the opening.

15. The sensor assembly according to claim 1, wherein the packaging structure is a molding material.

16. An electronic system comprising:
a control unit; and
a sensor assembly operative coupled to the control unit, the sensor assembly including:
a packaging body having a through opening that places an area internal to the packaging body in fluid communication with an environment external to the sensor assembly;
a first semiconductor chip that integrates a humidity sensor and a control circuit operatively coupled to the humidity sensor, the humidity sensor housed in the internal area to the packaging body and in fluid communication with the environment external to the sensor assembly through the opening; and
a second semiconductor chip that integrates a MEMS pressure sensor bonded to the first semiconductor chip, the pressure sensor housed inside the packaging body and in fluid communication with the environment external the sensor assembly through the opening, the pressure sensor operatively coupled to the control circuit.

17. The electronic system according to claim 16, wherein the package body includes a substrate and a cap.

18. The electronic system according to claim 16, wherein the opening is a first opening, the second semiconductor chip including a second opening at least partially aligned with the first opening, the first and second openings exposing the humidity sensor of the first semiconductor chip.

19. The electronic system according to claim 16, wherein the electronic system is at least one of a smartphone, tablet, and wearable device.

20. The electronic system according to claim 16, wherein the second semiconductor chip is arranged between the first semiconductor chip and a substrate.

21. A sensor assembly comprising:
a packaging structure including a substrate, a cap, and molding material, the packaging structure including a through opening;
a first semiconductor chip that integrates a humidity sensor and a control circuit, the control circuit being operatively coupled to the humidity sensor, the humidity sensor housed within the packaging structure such that the humidity sensor is in fluid communication with an environment external through the opening; and
a second semiconductor chip coupled to the first semiconductor chip, the second semiconductor chip integrating a pressure sensor that is operatively coupled to control circuit, the pressure sensor housed inside the packaging structure and in fluid communication with the environment external to the sensor assembly through the opening.

22. The sensor assembly according to claim 21, wherein the first semiconductor chip is arranged between the second semiconductor chip and the substrate.

23. The sensor assembly according to claim 21, wherein the opening is a first opening and provided in the substrate, and the first semiconductor chip includes a second opening at least partially aligned with the first opening.

* * * * *